(12) United States Patent
Kratzer et al.

(10) Patent No.: US 7,951,328 B2
(45) Date of Patent: May 31, 2011

(54) DEVICE AND METHOD FOR AUTOMATICALLY ANALYZING BLOOD SAMPLES

(75) Inventors: Michael Kratzer, Munich (DE); Volker Freiherr Von Der Goltz, Seeon (DE)

(73) Assignee: VDG-Von der Goltz GmbH, Seeon (DE)

( * ) Notice: Subject to any disclaimer, the term of this patent is extended or adjusted under 35 U.S.C. 154(b) by 1101 days.

(21) Appl. No.: 11/632,439

(22) PCT Filed: Jul. 12, 2005

(86) PCT No.: PCT/DE2005/001228
§ 371 (c)(1),
(2), (4) Date: Mar. 12, 2007

(87) PCT Pub. No.: WO2006/005326
PCT Pub. Date: Jan. 19, 2006

(65) Prior Publication Data
US 2007/0258859 A1    Nov. 8, 2007

(30) Foreign Application Priority Data

Jul. 12, 2004    (DE) .......................... 10 2004 033 654

(51) Int. Cl.
*G01N 21/00*    (2006.01)
*G01N 15/06*    (2006.01)

(52) U.S. Cl. ......................................... 422/63; 422/68.1
(58) Field of Classification Search .................... 422/63, 422/68.1
See application file for complete search history.

(56) References Cited

U.S. PATENT DOCUMENTS

| | | | | |
|---|---|---|---|---|
| 5,164,318 A | * | 11/1992 | Sato et al. | 435/286.4 |
| 5,460,779 A | * | 10/1995 | Kratzer et al. | 422/73 |
| 5,550,059 A | * | 8/1996 | Boger et al. | 436/54 |
| 5,902,253 A | * | 5/1999 | Pfeiffer et al. | 600/584 |

FOREIGN PATENT DOCUMENTS

| | | |
|---|---|---|
| DE | 2 131 423 | 6/1971 |
| EP | 0 522 256 A2 | 5/1992 |
| EP | 0 812 570 A1 | 5/1992 |

* cited by examiner

*Primary Examiner* — Lore Jarrett
(74) *Attorney, Agent, or Firm* — Karl F. Milde, Jr.; Eckert Seamans Cherin & Mellott, LLC

(57) ABSTRACT

A device for automatically analyzing blood samples includes an extraction station (I), where blood can be extracted from a storage vessel (40) by an extraction device (15); a measuring station (II), where the extracted blood can be passed via a head part (46) through an aperture (26) of an aperture holder (30) arranged in a measuring part (9), the measuring part (9) being connected to the head part (46); a receiving station (III), for receiving measuring parts (9) configured as disposable parts; and a device (3) for moving the extraction device (15) and the head part (46) between the extraction station (I), the measuring station (II) and the receiving station (III).

30 Claims, 4 Drawing Sheets

US 7,951,328 B2

DEVICE AND METHOD FOR AUTOMATICALLY ANALYZING BLOOD SAMPLES

BACKGROUND OF THE INVENTION

This invention relates to a device and method for automatically analyzing blood samples.

This device is derived from EP 0 522 256 B1, in which supply vessels filled with blood are simultaneously conveyed to a test head from a magazine device and a magazine aperture holder. The test head comprises a capillary holder to which at least one capillary is attached, which can be inserted into one of the supply vessels. Furthermore, the test head contains a head part, which can be moved between a first position of the capillary holder where an aperture holder is attached to the capillary holder, and a second position where the aperture holder is positioned between the capillary holder and the head part to permit passing the blood through the capillaries and the aperture of the aperture holder through capillaries dipped in a supply vessel. After completing a measuring procedure, the used aperture holder and the used supply vessel are removed from the test head by moving the head part into the first position. Subsequently, the test head is cleaned with the aid of an additional device.

SUMMARY OF THE INVENTION

The purpose of this invention is to considerably simplify this device for the automatic analyzing of blood samples, which will result in tests that are far more cost-effective. The invention also comprises a method for the implementation of the tests.

A significant advantage of this invention is the fact that this invention is structured in a far simpler manner and can therefore be operated more economically, as compared to the device described in EP 0 522 256 B1. This results in tests which are considerably more cost-effective. This is mainly attributable to the fact that only single-use or disposable measuring parts are used for connecting the aperture holder with the magazine device. This eliminates the need for using blood supply vessels from an additional magazine device due to the special design both of the head part as well as the measuring parts in this invention. Due to the fact that the device according to the invention is designed to permit the activation of the various stations, i.e. the blood extraction station, measuring station, a receiving station for substances affecting platelet formation or coagulation (for instance ADP), as well as a rinsing station and a disposal station in a pre-determined order, the head part as well as the test head which are used in the existing device, both of which have a very complicated design, can be eliminated. Furthermore, the elaborate activation and operation of these parts also become superfluous.

For a full understanding of the present invention, reference should now be made to the following detailed description of the preferred embodiments of the invention as illustrated in the accompanying drawings.

DESCRIPTION OF THE PREFERRED EMBODIMENTS

Figure 1:
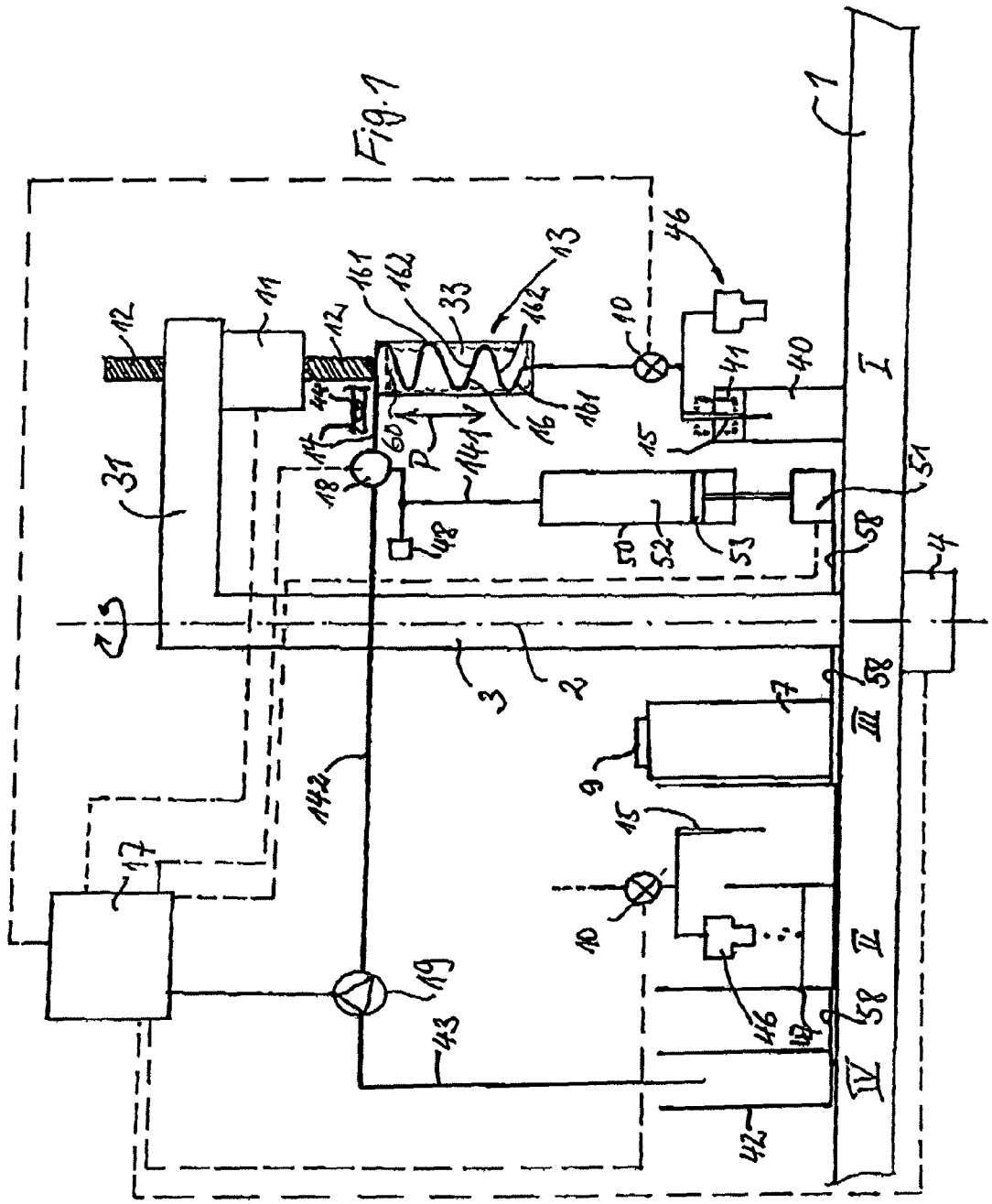
FIG. 1 is a schematic illustration of the device according to the invention.

The preferred embodiments of the present invention will now be described with reference to FIGS. 1-4 of the drawings. Identical elements in the various figures are designated with the same reference numerals.

Figure 2:
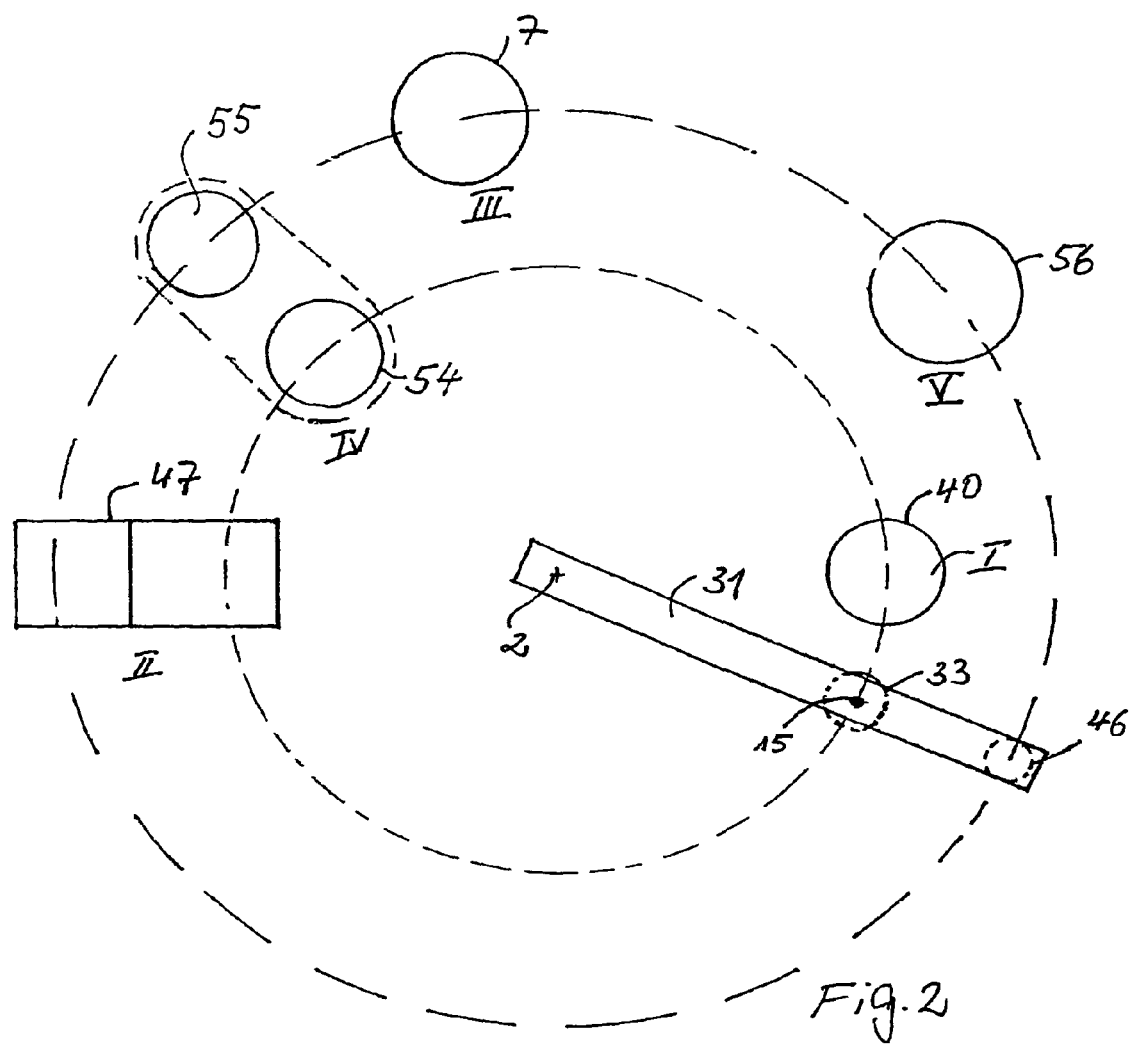
FIG. 2 is a top view of the device in FIG. 1.

According to FIGS. 1 and 2, this invention for automatically analyzing blood samples essentially comprises a rotating arm 31 on worktop 1 or on a different measuring surface, which can be swiveled around rotation axis 2 between several stations I, II and III and also between stations IV and V, if required.

The first station I is a blood extraction station, in which the blood is extracted from a supply vessel 40. Station II is a measuring station, in which blood removed from supply vessel 40 is conveyed for measuring through head part 46 in a manner explained later on, through the aperture of an aperture holder of measuring part 9 (FIG. 3), whereby measuring part 9 and head part 46 in measuring station II are firmly attached.

In receiving station III the measuring parts 9 designed to be single-use or disposable, which comprise aperture holder 25 (FIG. 3), as schematically depicted in FIG. 1 as measuring part 9 in magazine 7, are ready to be attached in sequence to the head part 46.

Furthermore, an intake station for a substance affecting platelet formation or coagulation as well as a rinsing station can be provided, as explained further on.

Rotating arm 3 is operated with the aid of the schematically depicted driving motor 4. Ideally, motor 4 should be a multiphase motor which can be set precisely to activate the individual stations.

The stations mentioned should preferably be located on a circular arc, as depicted in FIGS. 1 and 2. However, these stations could also be arranged in a straight line, in which case the rotating arm 3 would be operated in either a linear or an x-y direction.

As shown in FIG. 1, drive motor 11 is attached to swivel 31 of rotating arm 3, with the aid of which holding part 13 can be moved up and down, preferably in a vertical direction, towards the surface of worktop 1, as shown with arrow P. For practical reasons drive motor 11 has a conventional mechanism which can move threaded rod 12 in the direction of arrow P, with holding part 13 attached to the threaded rod.

Holding part 13, which is moved back and forth with the aid of drive motor 11 in the direction of arrow P, comprises needle part 15 and is located along the side facing worktop 1. On the side facing away from worktop 1 it is attached to a coil or spiral-shaped tubing 16 which is held in place by holding part 13. The side of the tubing facing away from needle part 15 is connected to duct 14, which is basically a hosepipe. The insides and/or outsides of tubing 16 and needle part 15 have a hydrophobic coating to ensure that aspirated blood components will not adhere to the inner and/or outer walls. Duct 16 and/or needle part 15 should be made from materials containing a hydrophobic or oleophobic coating, especially when the material is metal. The coating can be either a sol-gel-nanocomposite layer or a TEFLON-type fluoropolymer layer. In the case of needle part 15 this layer should also be applied to the outside.

Head part 46 should be positioned along holding part 13 spaced away from needle part 15, to provide an optional connection to measuring part 9, as will be explained later on. Needle part 15 and head part 46 are connected by valve part 10, which is activated by control unit 17 and can establish a connection between needle part 15 and tubing 16 or between head part 46 and tubing 16, as required.

Duct 14 leads to valve 18 which is activated by control unit 17, which can establish a connection to duct 141, which in turn is attached to a receiving reservoir in the form of piston/cylinder unit 50. This piston/cylinder unit 50 is operated by driving motor 51, which in turn is activated by control unit 17. Furthermore, valve 18 can establish a connection between duct 14 and duct 142, which is attached to a pump 19 leading to container 42 which is filled with a rinsing agent, preferably NaCl, via duct 43.

In station III it is preferable, if measuring parts 9 are guided by magazine device 7 in sequence into the motion path of rotating arm 3.

In addition to duct 16 which is attached to needle part 15, holding part 13 includes heating device 33, as depicted in FIG. 1, which is in the form of a metallic heating core, along which duct 16 is either coiled or twisted in the form of a spiral. The coiling arrangement depicted in FIG. 1 has the advantage that the upper and lower sides of sections 162, which are connected above curve 161, are always inverted in successive loops, as a result of which the blood is "tilted" or "tipped over" when traversing the sections. In this way a sedimentation of the blood can be avoided significantly, if not totally. Additional heating devices can be considered for measuring parts 46 and/or needle part 15, as explained later.

Figure 3:
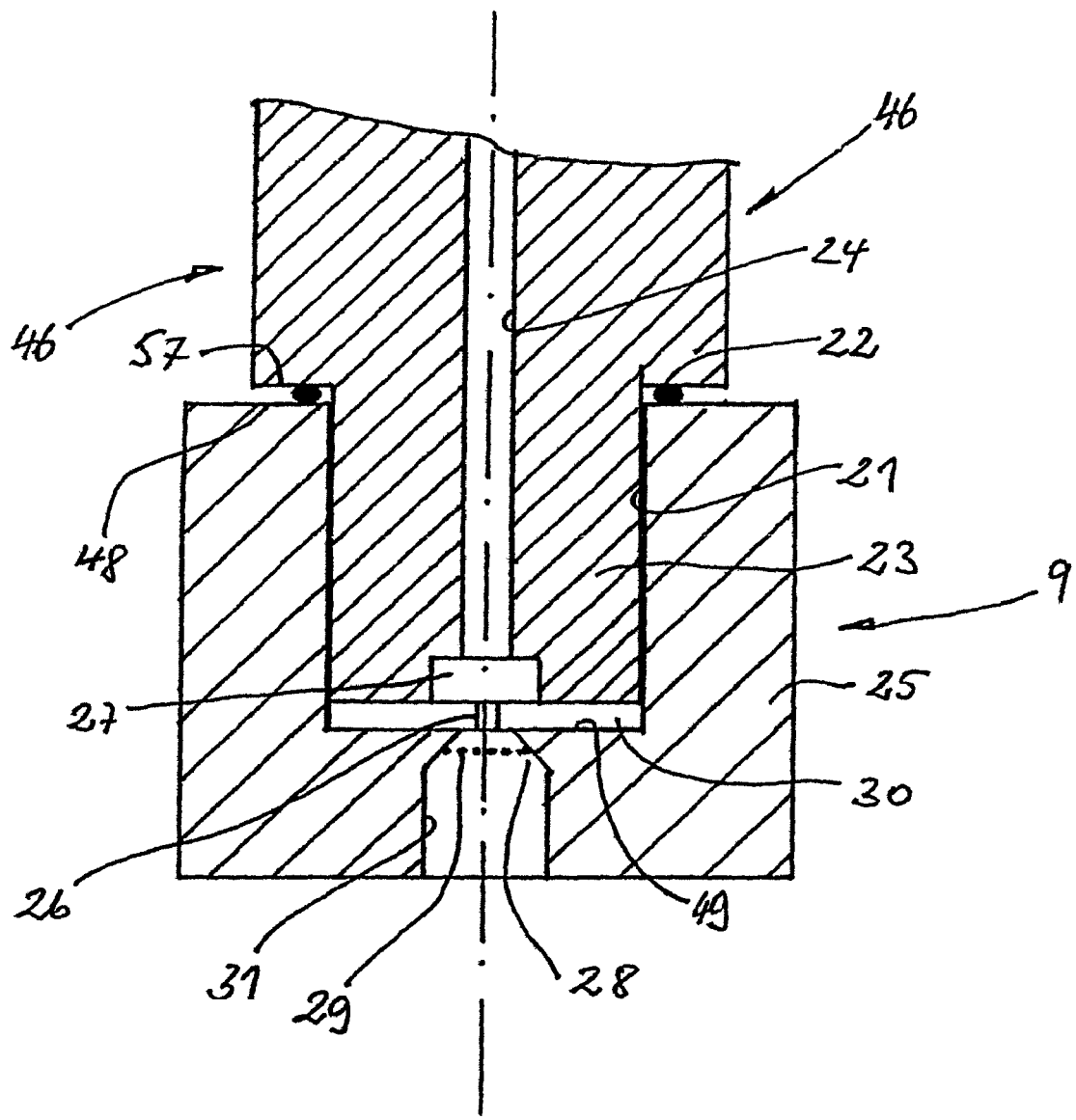
FIG. 3 is a side view of a measuring part for the device of FIG. 1 with an aperture holder as well as a head part inserted into the measuring part.

The following is a description of the design of the measuring part 9 and the head part 46 as depicted in FIG. 3. Head part 46 contains the lower section 23, which can be inserted firmly into recess 21 of measuring part 9. The seal between head part 46 and measuring part 9 is obtained by using an 0-seal 22 which is positioned along shoulder 57 of lower section 23, which ends up close to the device when the lower section 23 is positioned in recess 21 next to the shoulder 48 along the recess edge.

A slot opening 24, which may have the appearance of a capillary and is attached to the top of duct 16 through valve 10, runs through the head part 46. Slot opening 24 extends as far as an antechamber 27 at the lower end of the section 23. As described previously, aperture holder 30 is located at the lower base 49 of recess 21, adjacent to aperture 26 which faces slot opening 24. In the body part 25 of measuring part 9 a space is located behind aperture holder 30, which represents secondary chamber 28 and extends down into blood discharge chamber 31. With the aid of sealing mechanisms not described in detail here, the head part 46 and measuring part 9 can be firmly attached to one another by moving them towards one another, and they can be separated by moving them apart from one another.

When blood moves from duct 16 into the head part 46 and measuring part 9, the blood will flow into the aperture 26 of aperture holder 30 through slot opening 24 via antechamber 27 and subsequently into the secondary chamber 28 and the blood discharge chamber 31. In station II the blood discharged from blood discharge chamber 31 can be collected in receptacle 47.

The following is a description of the operation of the device according to the invention. This is based on the assumption that all parts and/or elements related to this invention which come into contact with blood, have been cleaned.

At first rotating arm 3 is moved to station I by driving motor 4 and driving motor 11 is activated to lower holding part 13 (arrow P). After needle part 15 has pierced the seal 41 of supply vessel 40 and has been dipped into the blood contained therein, piston 53 of piston/cylinder unit 50 is activated by driving motor 51. The seal should preferably be a rubber stopper.

In order to avoid sedimentations in supply vessel 40, a device not described in detail here is envisaged which would continuously move, invert or rotate supply vessel 40.

The system incorporating duct 16 as well as ducts 14, 141, 142, and 43 contain a neutral fluid such a rinsing liquid removed from container 42 via duct 43, which could be a physiological NaCl-solution, for instance. This would produce a separation medium between the aspirated blood and the fluid mentioned above, which is depicted as an enlarged air bubble 44 in FIG. 1 and should preferably be located in the area between valve 18 and duct 43. By operating pump 19 the aspirated blood can be agitated back and forth until it is time to do the measuring, in order to keep it moving and thus avoid sedimentation. We already pointed out the advantage of the winding design of duct 16. For the aspiration of blood described earlier, valve 18 establishes a connection between duct 16 and duct 141. In order to agitate the blood in this position, valve 18 of piston 53 in cylinder chamber 52 can be moved back and forth. Throughout this procedure the blood will be kept at the correct temperature of say 37° C. with the aid of heating device 33.

Rotating arm 3 is now moved towards station III and removes measuring part 9 from magazine device 7. For this purpose driving motor drive is activated first, in order to move rotating arm 3 to the top of magazine device 7. After that driving motor 11 is activated and head part 46 is lowered, until it can be firmly connected to the prepared measuring part 9 in the manner described earlier. When the pick-up of measuring part 9 has been completed, driving motor 11 is activated again, in order to lift head part 46 and the measuring part 9 attached to it and remove it from magazine device 7. We should like to point out that magazine device 7 can also have a different design. The magazine device may, for instance, include a conveyor belt or similar, with the aid of which measuring parts 9 can be transported to location III on a continuous basis, where they will be connected to head part 46.

Subsequently rotating arm 1 is moved to station II by driving motor 4. Now the actual measuring is carried out, whereby piston 53 of piston/cylinder unit 50 is moved in a way that ensures that the blood will flow continuously through aperture 26 of measuring part 9 and will leave through blood discharge chamber 31. Here valve 10 connects head part 46 with duct 16. Any blood dripping out of measuring part 9 is caught in receptacle 47. Throughout this measuring procedure, the volume flow of the blood is controlled by measuring the pressure with the aid of pressure sensor 48 and with the described procedure the movement of piston 53 is activated to ensure a specific pressure/volume flow characteristic. A thrombus is formed in aperture 26. Subsequently head part 46 is removed from measuring part 9 with the aid of driving motor 11 in the manner described above and measuring part 9 is discarded into receptacle 47.

After the measuring has been completed and the blood has been discarded, ducts 16 and 14 as well as needle part 15 must be washed with a detergent which should be removed from container 42 with the aid of pump 19 and then pumped through the tubing, ducts and needle part 15 with valve 10 in the appropriate position. With the aid of the hydrophobic and oleophobic coating mentioned earlier the cleaning can be accomplished speedily. In order to clean the outside of needle part 15 it must be moved to a special rinsing station IV by operating driving 4, where it is immersed in container 54 (FIG. 3) containing a detergent or rinsing agent with the aid of motor 11.

As the arm 31 is rotated around its axis 2 by a drive motor, the storage vessel of extraction station (I) and a magazine device for measuring parts in the receiving station (II) are separated by at least the difference between the two radii.

In order to clean measuring head 46, a rinsing agent is pumped through measuring head 46 with valve 10 in the appropriate position. In order to clean the outside of measuring head 46 it needs to be moved to station IV and immersed in container 55 (FIG. 2) containing a detergent or rinsing agent at the same time as needle part 15.

In station V measuring part 9, which is removed from magazine device 7, can be immersed in container 56 (FIG. 2), which may contain ADP or another liquid medium, that will reach the porous material of aperture holder 30 and the walls of aperture 26 when immersed, as mentioned earlier. This medium will affect the coagulation and/or aggregation of the blood flowing through aperture 26 in a predetermined manner during the measuring procedure.

Container 42 and driving motor 51 with piston/cylinder unit 50 should be screwed tightly onto rotating arm 3 with the aid of holding device 58.

According to FIG. 1 an additional heating device 60 attached to holding part 13 is envisaged, with the aid of which needle part 15 could be heated. This heating device 60, which is only illustrated schematically, could be either in the form of a heater which partially surrounds needle part 15 or a fan heater. A similar heating device can also be designed for head part 46.

Figure 4:
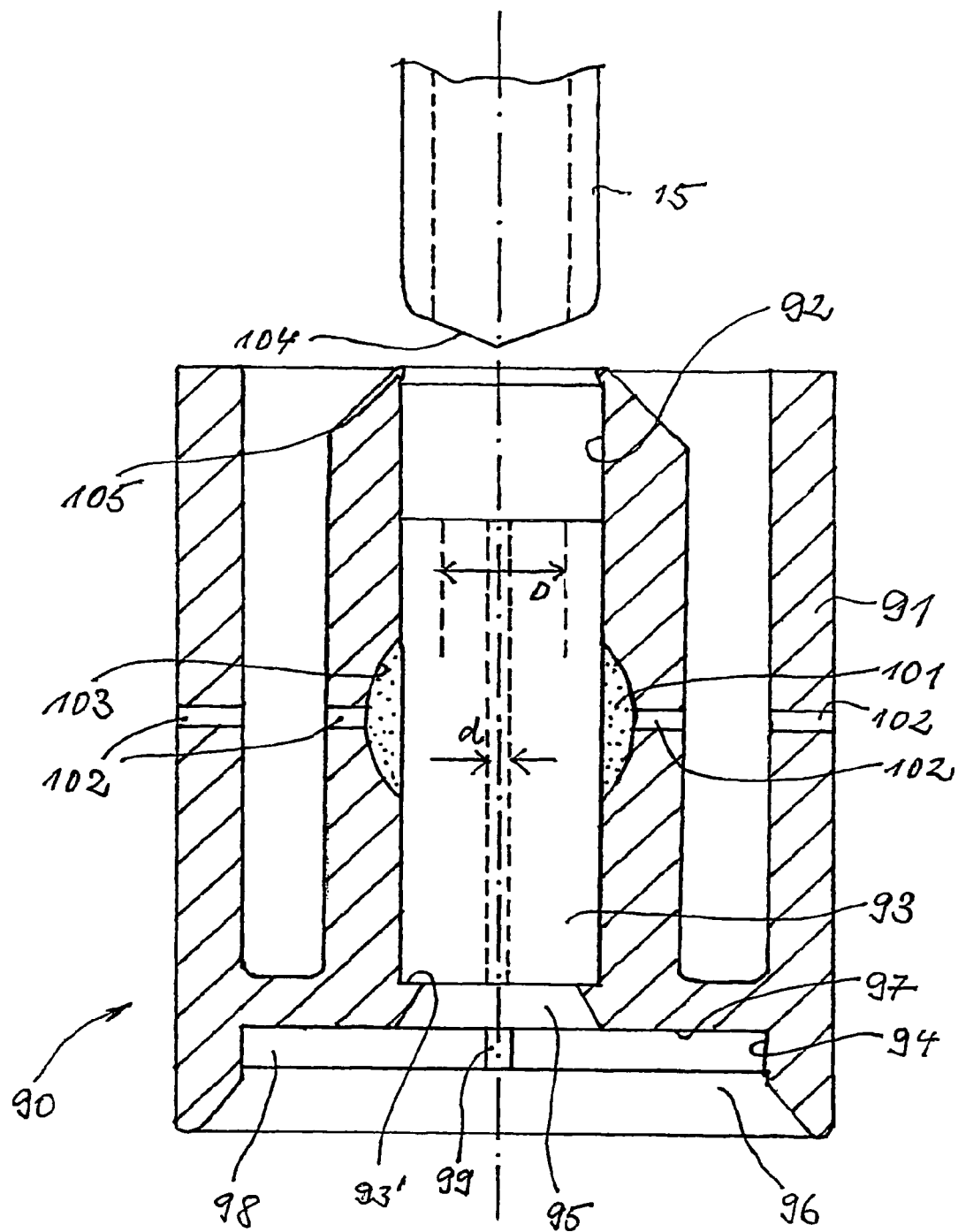
FIG. 4 is an additional preferred measuring part for the device of FIG. 1.

The following is a description of an additional preferred design for measuring part 90 which can be attached directly to needle part 15, in accordance with FIG. 4. In this way both head part 46 as well as valve 10 could be eliminated. Measuring part 90 contains a central opening 92 within body part 91 into and out of which needle part 15 could be conveyed with the aid of driving motor 11. A small tube 93, preferably with a borehole of 92, is located within the slot running in a longitudinal direction along body part 91, which extends up to the lower shoulder 93 between opening 92 and body part 91 as far as the adjacent antechamber. Antechamber 95 extends into an expanded area 94 of body part 91, which in turn opens onto secondary chamber 96 of body part 91, which serves as a blood discharge chamber. Aperture holder 98 is located along shoulder 97 between antechamber 95 and the expanded chamber 94 in a way which ensures a tight separation between antechamber 95 and secondary chamber 96. Aperture 99 of aperture holder 98 are thus connected by antechamber 95 and secondary chamber 96. The aperture holder 98 may be made from either porous or non-porous material.

The needle part 15 has a conical end part 104 on the side facing borehole 92, which can be inserted firmly into borehole 92. For this purpose borehole 92 contains a ring-shaped seal 105 at its upper end which may be in the form of a sealing flange or an o-seal. It is also possible to obtain a seal by providing the end-part of borehole 92 facing needle part 15 with the same conical design as 104 to achieve a tight seal.

Tube 93 may be either ring-shaped with a relatively large internal diameter D or, to emulate a capillary, it may have an appropriately small internal diameter d. The external diameter of the tube should be 0.8-2.0 mm and the internal diameter 150-500 μm.

Body part 91 consists of the single-use or disposable measuring part 90 made from plastic material, whereby aperture 98 can be firmly attached to shoulder 97 with ultrasound welding or adhesive.

Tube 93 should preferably be made from stainless steel or a fluorine material (e.g. Tefzel®). It is best attached with adhesive 101 on the inside of opening 92, whereby adhesive 101 can be injected into recess 103 intended as a space for adhesives, which is located within a channel running in a transverse direction of body part 91. The recess should ideally be ring-shaped, in order to ensure extra firmness and even adhesion.

Instead of the adhesion procedure described above, tube 93 can also be affixed by applying contact pressure to borehole 92.

In order to carry out the measuring procedure, blood is initially aspirated from reservoir 40 (station I) through needle part 15 in the previously described manner. After moving rotating arm 3 to receiving station III, needle part 15 is placed directly in measuring part 90 within magazine device 7 and firmly attached. After moving arm 3 towards measuring station II the previously aspirated blood is conveyed from needle part 15 into the slot opening or into borehole 92 and then transported to tube 93 or to borehole 92. It will then flow through antechamber 95 and aperture 99 until it reaches secondary chamber 96.

During the measuring procedure the alignment of needle part 15 and aperture 99 and the resulting blood flow may vary. The direction could, for instance, run from top to bottom or the reverse, or even horizontal. Other alignments can also be considered.

With an alternative design tube 93 may be eliminated altogether, in which case borehole 92 would have an internal diameter of 200-1000 μm.

There has thus been shown and described a novel device and method for automatically analyzing blood samples which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. Device for automatically analyzing blood samples, comprising, in combination:
    an extraction station, in which blood is extracted from a storage vessel by an extraction device;
    a measuring station having a measuring part that receives blood from the extraction device, said measuring station being operative to analyze blood samples by passing blood through an aperture in an aperture holder arranged in the measuring part;
    a receiving station for receiving measuring parts configured as disposable parts;
    a device for moving the extraction device between the extraction station and the measuring station as well as the receiving station,
    wherein the extraction device comprises:
    a needle part which can be connected to the measuring part;
    a head part, which can be connected to a measuring part provided in the receiving station, wherein in the extraction station blood can be drawn into the needle part from the storage vessel and in the measuring station blood can be conveyed to the measuring part through the head part;
    a valve arranged to permit an alternative connection to the needle part and the head part; and
    a holding part having a heating device for warming blood that is aspirated into a duct from the needle part.

2. Device of claim 1, wherein the device for moving the extraction device comprises a movable arm activated by a first drive motor.

3. Device of claim 2, wherein the arm can be conveyed to the extraction station, measuring station and receiving station with the aid of a stepper motor.

4. Device of claim 2, wherein the arm is rotatable about a rotation axis by the first drive motor and wherein the storage vessel of the extraction station and a magazine device for measuring parts in the receiving station are separated by a difference between a first and a second radius of the rotation axis.

5. Device of claim 4, wherein the needle part and the head part on the arm are arranged, radially displaced to one another, in accordance with the space between the storage vessel and the magazine device in relation to the rotation axis.

6. Device of claim 1, wherein the extraction station, the measuring station and the receiving station are arranged in close relationship and wherein an arm can be conveyed to the extraction station, the measuring station and the receiving station by a first drive motor.

7. Device of claim 6, wherein the first drive motor is a stepper motor which is activated for conveyance of the arm to the extraction station, the measuring station and the receiving station.

8. Device of 7, wherein a second drive motor is arranged on the arm for moving the holding part up and down, and wherein the holding part comprises the extraction device.

9. Device of claim 8, wherein the second drive motor comprises a screw and nut mechanism.

10. Device of claim 1, wherein the needle part, on the side facing away from the storage vessel, is attached to the duct that is held in place by the holding part and which, in turn and on the side facing away from needle part, is connected through a first valve to a blood reception reservoir; and further comprising a third drive motor for the aspiration of blood from the storage vessel into a reception reservoir or for the extraction of blood from the reception reservoir into the measuring part.

11. Device of claim 10, wherein the reception reservoir is a piston/cylinder unit actuated by the third drive motor.

12. Device of claim 10, wherein the duct and the needle part have at least one of an inner and outer hydrophobic coating.

13. Device of 10, wherein at least one of the duct and the needle part are made from a metal material with at least one of an inner hydrophobic and oleophobic coating.

14. Device of claim 13, wherein the coating is selected from the group consisting of a sol-gel-nanocomposite layer and a TEFLON-type fluoropolymer layer.

15. Device of claim 1, wherein the heating device is in the form of a metallic heating core, and the duct, in the heating device, is serpentine-shaped.

16. Device of claim 15, wherein the duct is arranged in such a way that the aspirated blood flows in a vertical direction when traversing the serpentine sections, in order to prevent a sedimentation of the blood.

17. Device of claim 1, wherein in the measuring station the blood is conveyed from the duct through the measuring part by activating the reception reservoir with a third drive motor through an aperture of the measuring part, after which the blood discharged from the measuring part is caught in a receptacle.

18. Device of claim 1, wherein the head part contains a section, which can be inserted tightly into a recess of the measuring part, wherein the head part has an opening slot connected to the duct which opens onto an antechamber in a section that is located adjacent to the bottom surface of a recess of the measuring part, wherein an aperture holder is so positioned on the bottom surface that the antechamber is connected with an aperture of the aperture holder after moving the section into the recess so that, as a result, the blood moved into antechamber via the opening slot is conveyed from the antechamber through the aperture into a blood extraction chamber, which is located in the measuring part along the side of the aperture facing away from antechamber.

19. Device of claim 18, wherein a seal between the head part and the measuring part is effected by applying an O-ring to a shoulder which is located on a side of a section facing away from the antechamber and which ends up close to a section along the edge of the recess when such section is moved into the recess of the measuring part.

20. Device of claim 1, wherein the measuring part contains an opening within a body part, which opens towards one side of the body part, wherein a borehole in the body part converges into an antechamber, which in turn converges into an expanded section, wherein a shoulder is positioned between the section and the antechamber, to which the aperture holder is closely attached, wherein a secondary chamber opening towards the other side of the body part lies adjacent to the section, and wherein the antechamber and the secondary chamber are closely connected through the aperture of the aperture holder and the needle part can be inserted tightly into the borehole.

21. Device of claim 20, wherein the needle part includes a conical section along a side facing the borehole which serves as an entrance conveyor and wherein the borehole includes a sealing element along a side facing the needle part which forms a tight connection between the borehole and the needle part inserted therein.

22. Device of claim 21, wherein the sealing element is at least one of an O-ring and a sealing flange.

23. Device of 20, wherein the aperture holder is attached to the shoulder by at least one of ultrasound welding and an adhesive.

24. Device of claim 20, wherein a small tube is tightly attached to the borehole, through which blood flows from the borehole to the aperture.

25. Device of claim 24, wherein the tube is either glued to the inner wall of the borehole or affixed thereto by contact pressure.

26. Device of claim 24, wherein the external diameter of the tube is in the range of 0.8 to 2.0 mm.

27. Device of claim 24, wherein the internal diameter of the tube is in the range of 150-500 µm.

28. Device of claim 1, wherein the tube is made from at least one of stainless steel and a fluorine plastic material.

29. Device of claim 1, further comprising a rinsing station which can be accessed by an arm, which comprises a container with a detergent for rinsing that can be pumped and conveyed to the duct and the extraction device via a section of the duct.

30. Device of claim 29, further comprising an additional rinsing station which can be accessed by the arm, wherein the needle part and the measuring part can be dipped in a container filled with at least one of a rinsing agent and a detergent by operating a second drive motor, in order to clean external sides thereof.

* * * * *